United States Patent
Wasily et al.

(10) Patent No.: US 11,297,050 B2
(45) Date of Patent: Apr. 5, 2022

(54) SECURE COMMUNICATION FOR MEDICAL DEVICES

(71) Applicant: Thirdwayv, Inc., Irvine, CA (US)

(72) Inventors: Nabil Wasily, Foothill Ranch, CA (US); Andrew P. Lentvorski, San Diego, CA (US)

(73) Assignee: THIRDWAYV, INC., Irvine, CA (US)

( * ) Notice: Subject to any disclaimer, the term of this patent is extended or adjusted under 35 U.S.C. 154(b) by 98 days.

(21) Appl. No.: 16/036,750

(22) Filed: Jul. 16, 2018

(65) Prior Publication Data

US 2019/0020641 A1 Jan. 17, 2019

Related U.S. Application Data

(60) Provisional application No. 62/533,567, filed on Jul. 17, 2017.

(51) Int. Cl.
| | |
|---|---|
| *H04L 29/06* | (2006.01) |
| *H04L 9/32* | (2006.01) |
| *G16H 80/00* | (2018.01) |
| *H04W 12/06* | (2021.01) |
| *G06F 21/44* | (2013.01) |
| *G06F 21/73* | (2013.01) |

(Continued)

(52) U.S. Cl.
CPC ............ *H04L 63/083* (2013.01); *G06F 21/35* (2013.01); *G06F 21/44* (2013.01); *G06F 21/57* (2013.01); *G06F 21/73* (2013.01); *G16H 80/00* (2018.01); *H04L 9/3213* (2013.01); *H04L 9/3218* (2013.01); *H04L 9/3263* (2013.01); *H04L 9/3268* (2013.01); *H04L 63/0823* (2013.01); *H04L 63/0876* (2013.01); *H04L 63/10* (2013.01); *H04W 12/06* (2013.01); *G16H 10/60* (2018.01); *G16H 40/40* (2018.01); *G16H 40/63* (2018.01); *G16H 40/67* (2018.01)

(58) Field of Classification Search
CPC . H04L 63/083; H04L 9/3218; H04L 63/0876; H04L 63/0823; H04L 9/3268; H04L 9/3213; H04L 9/3263; H04L 63/10; H04W 12/06; G06F 21/44; G06F 21/73; G06F 21/57; G06F 21/35; G16H 80/00
See application file for complete search history.

(56) References Cited

U.S. PATENT DOCUMENTS

| | | | |
|---|---|---|---|
| 9,980,140 B1 * | 5/2018 | Spencer | ................ A61M 5/172 |
| 2005/0071630 A1 * | 3/2005 | Thornton | ............ H04L 63/0823 |
| | | | 713/156 |

(Continued)

*Primary Examiner* — Robert B Leung
*Assistant Examiner* — Bruce S Ashley
(74) *Attorney, Agent, or Firm* — Snell & Wilmer LLP

(57) ABSTRACT

Methods, systems, and apparatus for providing secure communication. The device includes a trusted environment having a memory that is configured to store an application. The device includes one or more processors configured to perform operations of the application that execute within the trusted environment. The operations include sending an access request to connect with a second device, receiving an authentication request from the second device that requests the application to provide a zero-knowledge password proof and obtaining the zero-knowledge password proof. The operations also include sending the zero-knowledge password proof to the second device and establishing a communication channel with the second device.

20 Claims, 4 Drawing Sheets

(51) Int. Cl.
*G06F 21/57* (2013.01)
*G06F 21/35* (2013.01)
*G16H 10/60* (2018.01)
*G16H 40/40* (2018.01)
*G16H 40/67* (2018.01)
*G16H 40/63* (2018.01)

(56) References Cited

U.S. PATENT DOCUMENTS

| | | | |
|---|---|---|---|
| 2011/0081888 A1* | 4/2011 | Waniss | H04M 1/72527 455/411 |
| 2012/0060030 A1* | 3/2012 | Lamb | G06F 21/57 713/166 |
| 2014/0032733 A1* | 1/2014 | Barton | H04L 63/0853 709/223 |
| 2014/0364056 A1* | 12/2014 | Belk | H04B 5/0031 455/41.1 |
| 2014/0365781 A1* | 12/2014 | Dmitrienko | G06F 21/34 713/185 |
| 2016/0359636 A1* | 12/2016 | Kreft | G06F 21/45 |
| 2017/0109512 A1* | 4/2017 | Bower | G06F 21/32 |
| 2017/0319861 A1* | 11/2017 | Golden | A61B 5/7465 |

* cited by examiner

SECURE COMMUNICATION FOR MEDICAL DEVICES

CROSS-REFERENCE TO RELATED APPLICATIONS

This application claims priority to and the benefit of U.S. Provisional Patent Application No. 62/533,567 titled "SECURE COMMUNICATION FOR MEDICAL DEVICES," filed on Jul. 17, 2017, and the entirety of which is hereby incorporated by reference herein.

BACKGROUND

1. Field

This specification relates to a system, a device and/or a method for secure communication between a personal device, such as a smartphone, a tablet, a laptop or other computer, with another device, such as a medical device.

2. Description of the Related Art

Conventionally, patients, doctors, nurses and other healthcare professionals use a dedicated device to interact with a single medical device, such as a continuous glucose monitor (GCM), an artificial pancreas (AP) system, a pacemaker or an insulin unit (or "POD"). The dedicated device may have a single function or use, such as the control of the GCM or control of the POD. Since the dedicated device has a single function or use, multiple dedicated devices are necessary to address multiple healthcare issues. The use of multiple dedicated devices adds complexity and cost in managing a patient's overall health. Thus, patients, doctors, nurses and other healthcare professionals are transitioning from the use of multiple dedicated devices to the use of smartphones and other multi-use, multi-function personal devices.

These personal devices may run multiple applications that control and interact with the multiple medical devices. Since the personal device runs multiple applications in the same environment, e.g., using the same resources, as the medical applications that operate the medical devices, the medical applications are susceptible to various cybersecurity risks, such as malware, viruses and other vulnerabilities.

Accordingly, there is a need for a system, a method and/or a device that secures the medical applications and communication between the medical applications and medical devices.

SUMMARY

In general, one aspect of the subject matter described in this specification is embodied in a device, a system and/or an apparatus for providing secure communication. The device includes a trusted environment having a memory that is configured to store an application. The device includes one or more processors configured to perform operations of the application that execute within the trusted environment. The operations include sending an access request to connect with a second device. The operations include receiving an authentication request from the second device that requests the application to provide a zero-knowledge password proof. The operations include obtaining the zero-knowledge password proof. The operations include sending the zero-knowledge password proof to the second device. The operations include establishing a communication channel with the second device.

These and other embodiments may optionally include one or more of the following features. The device may include an untrusted environment. The untrusted environment may have a network access device. The network access device may establish a communication channel with the second device.

The processor may encrypt the zero-knowledge password proof prior to sending the zero-knowledge password proof to the second device. The zero-knowledge password proof may be a password that is provisioned during manufacturing, packaging or distribution. The processor may obtain from a server the certificate or the cloud authentication token. The cloud authentication token may be provisioned during manufacturing, distribution or packaging. The processor may send the certificate or the cloud authentication token to the second device. The processor may establish communication with the second device using the certificate or the cloud authentication token. The certificate may include an immutable identifier that is verified by the second device. The certificate may be signed by the server using a private key or other signature authority. The immutable identifier may include at least one of an International Mobile Equipment Identity (IMEI) number, a phone number, a Bluetooth Low Energy (BLE) Media Access Control (MAC) address, a TrustZone Identifier (ID) or other identifier.

The device may have a secure element. The trusted environment may be within the secure element. The processor may obtain, from the server, the certificate and store the certificate in the memory. The processor may revoke the certificate after a period of time and renew the certificate with the server after the certificate is revoked.

In another aspect, the subject matter is embodied in a medical device. The medical device includes a memory. The medical device includes one or more processors. The one or more processors execute instructions stored in the memory and perform operations. The operations include sending an authentication request to a mobile device. The operations include receiving at least one of a zero-knowledge password proof, a certificate or a cloud authentication token from the mobile device. The operations include authenticating the at least one of the zero-knowledge password proof, the certificate or the cloud authentication token from the mobile device. The operations include establishing communication with the mobile device.

In another aspect, the subject matter is embodied in a method for securely communicating between a medical device and an application on a personal device in a secure computing environment. The method includes by a medical device, an access request, and in response to receiving the access request, sending, by a processor of the medical device and to the personal device, an authentication request that requests multiple authentication factors. The method includes receiving, by the processor, multiple authentication factors. The method includes authenticating, by the processor, the multiple authentication factors. The method includes establishing by the processor and the application on the personal device, a chain of trust between the medical device and the personal device. The method includes establishing, by the processor and the application on the personal device, a secure communication channel between the medical device and the personal device based on the chain of trust.

BRIEF DESCRIPTION OF THE DRAWINGS

Other systems, methods, features, and advantages of the present invention will be or will become apparent to one of ordinary skill in the art upon examination of the following figures and detailed description. It is intended that all such additional systems, methods, features, and advantages be included within this description, be within the scope of the present invention, and be protected by the accompanying claims. Component parts shown in the drawings are not necessarily to scale, and may be exaggerated to better illustrate the important features of the present invention. In the drawings, like reference numerals designate like parts throughout the different views, wherein:

DETAILED DESCRIPTION

Disclosed herein are systems, devices and methods for securing communication between a personal mobile device, such as a personal device manager (PDM), and a medical device, such as a continuous glucose monitor (GCM), an artificial pancreas (AP) system, a pacemaker or an insulin unit (or "POD"). The secure communication system has a personal device, such as a smartphone, a tablet, a personal device manager (PDM) or other handheld or mobile device, which runs a software application that controls, manages and/or otherwise interacts with a medical device. The secure communication system establishes a secure communication channel among the personal device, the medical device and/or the server to ensure that commands, communication and/or other instructions among the devices are secure and protected from viruses, malware, and other security vulnerabilities. This creates a root or a chain of trust that ensures that the commands or other instructions that control the medical device are valid to prevent malicious control of the medical device. Moreover, the use of the personal device instead of a dedicated device to control the medical device allows for the patient, doctor, nurse or other healthcare professional to manage multiple medical devices to control different treatments from a single device. This reduces the overall healthcare cost of the patient, increases convenience and simplifies the control of multiple devices.

Other benefits and advantages include the use of a trusted execution space on the personal mobile device to create a trusted environment. The trusted execution space secures the medical application on the personal mobile device from security vulnerabilities residing on the personal mobile device due to other untrusted applications. The trusted execution space may be a logical and/or a physical separation that protects the operation of the medical application running on the personal mobile device and prevents the risk of exposure to the medical device.

Additionally, since the medical application and implementation is designed to interact with a medical device, the implementation minimizes the amount of resources necessary to secure communication.

Figure 1:
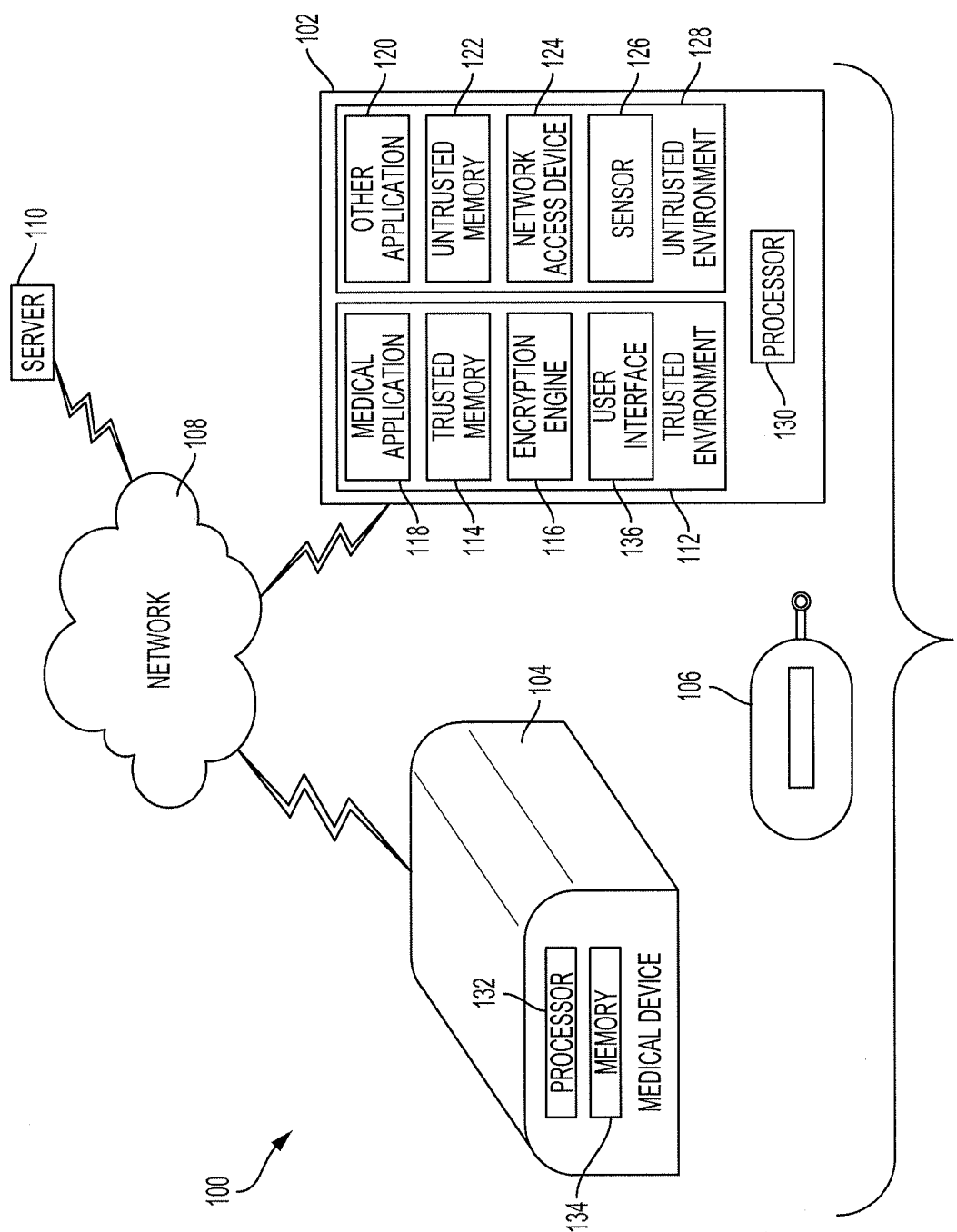
FIG. 1 shows an example block diagram of a secure communication system that establishes secure communication between a personal device and a medical device according to an aspect of the invention.

FIG. 1 shows an example block diagram of a secure communication system 100 that establishes secure communication between a personal device 102 and a medical device 104. The secure communication system 100 includes a personal device 102 and a medical device 104. The secure communication system 100 may include a hardware device 106, a network 108 and/or a server 110. The different components, such as the personal device 102, the medical device 104, the server 110 and/or the hardware device 106 may interconnect among each other through the network 108.

The secure communication system 100 includes the personal device 102. The personal device 102 may have a medical application 118 and other applications 120 loaded on the personal device 102. The medical application 118 controls, manages, communicates and/or otherwise interacts with the medical device 104. The personal device 102 may download the medical application 118 from the server 110. The personal device 102 may use a single medical application 118 to control multiple medical devices and/or have multiple medical applications 118 that each controls a corresponding medical device 104.

The personal device 102 has a trusted execution environment ("trusted environment") 112. The personal device may have an untrusted environment 128. The personal device 102 includes a medical application 118, a trusted memory 114, an encryption engine 116 and a user interface 136 within the trusted environment. The personal device 102 may include other applications 120, an untrusted memory 122, a network access device 124 and/or a sensor 126 within the untrusted environment 128. The components within the trusted environment 112 are isolated from the components within the untrusted environment 128. The trusted environment 112 may run a separate and/or a distinct operating system and have distinct resources from the untrusted environment 128. The trusted environment may establish a trust zone with a unique identifier that may be an immutable identifier.

The trusted environment 112 is a secure environment that is logically and/or physically separated and/or sandboxed from shared resources on the personal device 102. The trusted environment 112 is a dedicated secure environment that has resources, such as a trusted memory 114 and/or an encryption engine 116, that are dedicated for the exclusive use of the medical application 118 that resides within the trusted environment 112. The trusted environment 112 sandboxes the medical application 118, the trusted memory 114 and the encryption engine 116 from any of the other applications 120 or other resources on the personal device 102.

The personal device 102 has a medical application 118 within the trusted environment 112. The medical application 118 controls, manages, communicates or otherwise interacts with a medical device 104. For example, the medical application 118 may have or use a user interface 136 that receives input from a user, such as a patient, a doctor, a nurse or other healthcare professional to control or schedule the medical device 104 to dispense or administer medication or the application of treatment. The medical application 118 may communicate with the medical device 104 to dispense or administer the medication or the application of the treatment. In some implementations, the medical application 118 may have a portion of the application residing within the untrusted environment or may interface or connect with other applications and/or components within the untrusted environment 128.

The medical application 118 may be provisioned or downloaded via the server 110 including any certificates that include one or more immutable identifiers. When the medical application 118 is downloaded or provisioned, the medical application 118 may include a public key and/or a private key. The medical application 118 may send the public key to the server 110, which may ensure that the medical application 118 sending the public key is authorized to use the public key. The server 110 may validate the medical application 118, validate the integrity of the operating system of the personal device 102 and/or perform other operations to ensure the integrity within the trusted environment 112 and sign the public key once authentication is complete. This ensures that the original operating system has not been modified.

The medical application 118 may be stored in the trusted memory 114. The trusted memory 114 may be within the trusted environment 112. The trusted memory 114 may be a separate physical memory from the untrusted memory 122 or may be the same physical memory as the untrusted memory 122 but logically separated from the untrusted memory 122. The logical and/or the physical separation protects the trusted memory 114 from malware, spyware, viruses and/or other vulnerabilities residing within the untrusted memory 122 and prevents access to the trusted memory 114 by any other application. The trusted memory 114 may store instructions to execute on the processor 130 and may include one or more of a RAM or other volatile or non-volatile memory. The trusted memory 114 may be a non-transitory memory or a data storage device, such as a hard disk drive, a solid-state disk drive, a hybrid disk drive, or other appropriate data storage, and may further store machine-readable instructions, which may be loaded and executed by the processor 130.

The medical application 118 may interact and be connected with an encryption engine 116. The encryption engine 116 may reside within the trusted environment 112. Since the medical application 118 transmits and/or communicates to the medical device 104 using the network access device 124, which resides within the untrusted environment 128, the medical application 118 uses the encryption engine 116 to encrypt any transmissions and/or communications prior to delivering the transmissions and/or communications to the components within the untrusted environment 128. This ensures the integrity and confidentiality of the transmission and/or communication during transit to the medical device 104.

The encryption engine 116 may use a lightweight encryption algorithm, which facilitates decryption by the medical device 104. Since the processor 132 or controller of the medical device 104 does not have significant processing power, the lightweight encryption algorithm allows the medical device to decrypt the transmission and/or communication faster and also requires less processing power for decryption.

The medical application 118 may include, interface and/or interact with the user interface 136. The user interface 136 may be within the trusted environment 112, and thus, be a trusted component. That is, a component within the trusted environment 112, which is segregated, segmented or otherwise sandboxed or isolated from vulnerabilities within the untrusted environment 128. The user interface 136 may include any device capable of receiving user input, such as a button, a dial, a microphone, a graphical user interface or a touch screen, and any device capable of output, e.g., a display, a speaker, or a refreshable braille display. The user interface 136 allows a user to communicate with the medical application 118. For example, the user may be able to provide data to the medical application 118, such as user input, and/or receive feedback from the medical application 118 via the user interface 136. The input may include critical input, such as control and/or administration of the treatment and/or medication. The user interface 136 may display notifications and/or confirmations, e.g., to activate or deactivate the medical device 104. The user interface 136 may display a secret phase/image to protect the user from phishing attacks.

The personal device 102 includes a processor 130. The processor 130 may be a single processor or multiple processors. The processor 130 may receive data from one or more components and control the operations of the one or more components based on the received or determined data. For example, the processor 130 may run the medical application 118 to control a medical device 104 by transmitting commands and/or instructions from the medical application 118 to the medical device 104 through untrusted components, such as the network access device 124. The processor 130 may reside within the trusted environment 112, the untrusted environment 128 or both. For example, portions of the processor 130 may be within the trusted environment 112 and logical and/or physically segregated from other portions of the processor 130 within the untrusted environment 128. In some implementations, the processor 130 may be multiple processors, such as a dual processor, where at least one processor resides within the trusted environment 112 and at least one other processor resides within the untrusted environment 128.

The personal device 102 may have an untrusted environment 128. The untrusted environment 128 may use shared resources for all the other applications 120 and may be segregated, logically, physical or both, from the trusted environment 112. Since the untrusted environment 128 shares resources among all the other applications 120, the shared resources, the other applications 120 and any other communications and/or instructions that traverse the untrusted environment may be susceptible to vulnerabilities.

The other applications 120 may be within the untrusted environment 128. The other applications 120 may include a web browser, a mobile game, a social networking application or other mobile user application(s) designed to operate on the personal device 102. These other applications 120 may be downloadable from an online store but may be unrelated to the control and/or operations of the medical device 104 and may have not undergone security testing and verification. Thus, these other applications 120 may be susceptible to application level vulnerabilities, network level vulnerabilities, operating system level vulnerabilities or other vulnerabilities. The other applications 120 reside within the untrusted memory 122.

The untrusted memory 122 is a separate memory from the trusted memory 114 and may reside within the untrusted environment 128. The untrusted memory 122 may be logically and/or physically separated from the trusted memory 114 to maintain the security of the trusted memory 114. The untrusted memory 122 may store instructions to execute on the processor 130 and may include one or more of a RAM or other volatile or non-volatile memory. The untrusted memory 122 may be a non-transitory memory or a data storage device, such as a hard disk drive, a solid-state disk drive, a hybrid disk drive, or other appropriate data storage, and may further store machine-readable instructions, which may be loaded and executed by the processor 130.

The personal device 102 uses the network access device 124 to establish a connection with the medical device 104. The medical application 118 may send a command and/or an instruction using the network access device 124 to the medical device 104 through the network 108. Since the network access device 124 resides within the untrusted environment 128, the medical application 118 uses the encryption engine 116 to encrypt, sign or otherwise secure the command and/or instruction to ensure that the message is not modified or otherwise accessed prior to using the network access device 124 to send the message.

The network access device 124 may include a communication port or channel, such as one or more of a Wi-Fi unit, a Bluetooth® unit, a radio frequency identification (RFID) tag or reader, or a cellular network unit for accessing a cellular network (such as 3G or 4G). The network access device 124 may transmit data to and receive data from devices and systems not directly connected to the personal device 102. For example, the medical application 118 may communicate with the medical device 104 and/or the server 110 through the network 108.

The personal device 102 may have one or more sensors 126. The one or more sensors 126 may be within the trusted environment 112 and/or the untrusted environment 128. The one or more sensors 126 may include a proximity sensor. The proximity sensor may detect or measure a distance between the personal device 102 and the medical device 104. If the distance is less than a threshold distance, the proximity sensor may indicate to the processor 130 that the personal device 102 is within proximity to or within a threshold distance of the medical device 104. The processor 130 may allow for the authentication process between the personal device 102 and the medical device 104 to begin in order to establish a connection between the personal device 102 and the medical device 104.

The network 108, such as Bluetooth Low Energy (BLE) network, a local area network (LAN), a wide area network (WAN), a cellular network, the Internet, or combination thereof, connects the personal device 102 to the one or more medical devices 104 and/or the server 110. The server 110 may store a cloud authentication token, a database on immutable identifiers and/or certificates and/or other verification database to verify the validity and/or authenticity of one or more authentication factors. The server 110 may be a trusted application management (TAM) server, for example. When the personal device 102 connects with the medical device 104, the personal device 102 and the medical device 104 may not rely on the standard authentication methods, but instead, the personal device 102 and the medical device 104 may rely on an added upper layer authentication that runs on top of the network communication.

The secure communication system 100 may include a hardware device 106. The hardware device 106 may be a smartwatch, a fitness tracker, the medical device 104 or another device with an embedded hardware secure element. An embedded hardware secure element is a secure element chip that has anti-tamper and anti-cloning features. The embedded hardware secure element may have a security stack, key and certificate storage, secure boot verification and/or a device identifier.

The hardware device 106 may interact with the medical device 104 to provide to the medical device 104 one or more authentication factors, such as a hardware token, to authenticate the personal device 102. The hardware device 106 may be provided to the user and may need to be in proximity to the medical device 104 to provide the one or more authentication factors to the medical device 104. The hardware device 106 may transmit a hardware authentication token to the medical device 104 when the hardware device 106 is in proximity to the medical device 104. The hardware device 106 may have a hardware secure element that stores one or more certificates, such as the certificate for the medical application 118 of the personal device 102, and/or passwords, which is communicated, e.g., as a hardware authentication token, to the medical device 104 as an authentication factor. The hardware device 106 may have a user interface that allows the password to be entered.

The secure communication system 100 includes a medical device 104. The medical device 104 may be a as a continuous glucose monitor (GCM), an artificial pancreas (AP) system, a pacemaker or an insulin unit (or "POD") or other medical device that administers treatment, dispenses medication or performs other medical functions or procedures on a patient.

The medical device 104 may include a processor 132 and/or a memory 134. The processor 132 may be a single processor or multiple processors. The processor 130 may receive data from one or more components and control the operation of the one or more components based on the received or determined data. For example, the processor 132 may communicate with the medical application 118 and control the medical device 104. The processor 132 may transmit a response to the medical application 118 and verify one or more authentication factors sent by the medical application 118. The processor 132 may receive instructions from the medical application 118 and control the medical device 104. The processor 132 may perform decryption of the transmission and/or communication. The processor 132 may use a server secret to authenticate, encrypt and/or decrypt secure over-the-air firmware updates. The processor 132 verifies a firmware signature on the firmware to securely boot the firmware on the medical device 104.

The memory 134 may be a non-transitory memory or a data storage device, such as a hard disk drive, a solid-state disk drive, a hybrid disk drive, or other appropriate data storage, and may further store machine-readable instructions, which may be loaded and executed by the processor 132. The memory 134 may store a firmware update to the medical device 104, which is used to securely boot the medical device 104.

Figure 2:
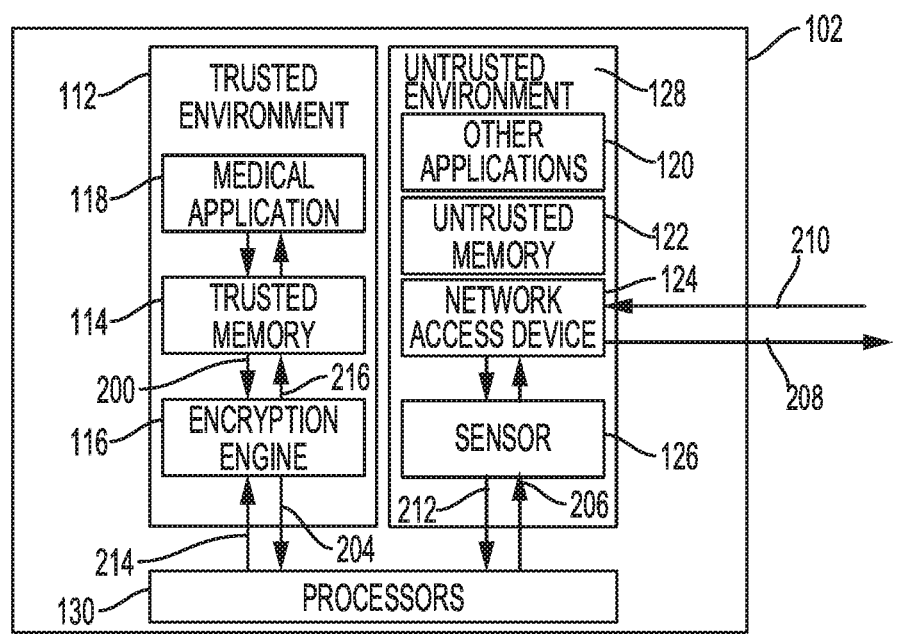
FIG. 2 shows an example personal device and the secure communication channels within the personal device according to an aspect of the invention.

FIG. 2 shows an example personal device 102 and the secure communication within the personal device 102. The medical application 118 resides within the trusted environment 112, which is a self-contained environment. The trusted environment 112 sandboxes or isolates the components, such as the medical application 118, the trusted memory 114 and the encryption engine 116, from other resources, such as other applications 120. This protects the medical application 118 from malware, spyware, viruses or other vulnerabilities directed at and/or within other resources.

The medical application 118 uses a trusted memory 114 that is separated from and is not shared with the other resources. This dedicated memory ensures that the medical application 118 resides within a clean environment, i.e., an environment free from malware, spyware, viruses, root kits or other vulnerabilities. Moreover, the medical application 118 may send any and all communications, commands and/or instructions along path 200 to the encryption engine 116 prior to transmission and/or communication to the medical device 104. The path 200 resides entirely within the trusted environment 112, and so, the transmission and/or communication may be in plain text and still maintain integrity without concern for any tampering or modification. The encryption engine 116, which resides within the trusted environment 112, encrypts the transmission and/or communication prior to sending the communication to the network access device 124 for transmission to the medical device 104. The encryption of the transmission and/or communication, while within the trusted environment, ensures integrity and confidentiality of the transmission and/or communication.

The encryption engine 116 provides the encrypted transmission and/or communication through the processor 130 along the paths 204, 206 to the network access device 124 to be transmitted out along the path 208 to the medical device 104. While the transmission and/or communication transmits through the untrusted environment 128 and the network 108, which are unprotected and susceptible to malicious attacks, the encryption protects the confidentiality and integrity of the transmission and/or communication. This prevents unauthorized modification, tampering and/or access to the transmission and/or communication.

The network access device 124 may receive an encrypted transmission and/or communication from the medical device 104 along the path 210 and pass the encrypted transmission and/or communication through the processor 130 to the encryption engine 116 via the paths 212, 214. The encryption engine 116 decrypts the transmission and/or communication prior to sending the transmission and/or communication to the medical application 118 along the path 216.

Figure 3:
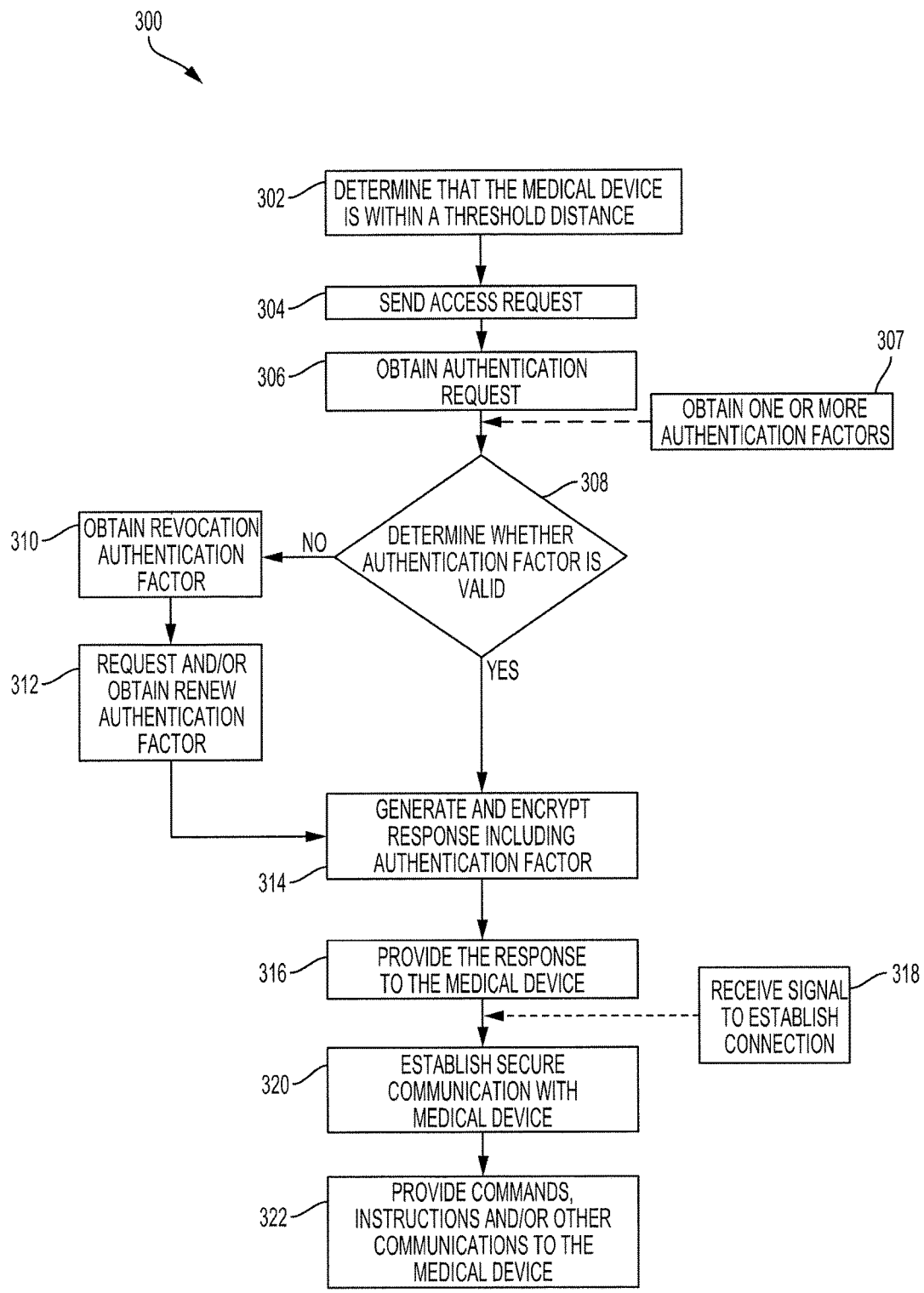
FIG. 3 is a flow diagram of an example process implemented by the personal device to securely connect with the medical device according to an aspect of the invention.

FIG. 3 is a flow diagram of a process 300 implemented on the personal device 102 to securely connect with the medical device 104. The one or more computers or data processing apparatuses, for example, the processor 130 in conjunction with other components, such as the medical application 118, of the secure communication system 100 of FIG. 1, appropriately programmed, may establish a secure connection between the personal device 102 and the medical device 104.

The personal device 102 may determine that the personal device 102 is within proximity or within a threshold distance of the medical device 104 (302). The personal device 102 may use a sensor 126, such as a proximity sensor, to measure a distance to the medical device 104 and determine that the distance is less than the threshold distance. In some implementations, the sensor 126 may detect whether the medical device 104 is within the threshold distance. The proximity sensor may transmit, for example, an electromagnetic field or an electromagnetic beam and look for changes in the field or a return signal. In some implementations, the network access device 124 may passively discover, scan or search for the medical device 104 and attempt to pair with the medical device 104 when the medical is discovered.

The personal device 102 may send an access request to the medical device 104 (304). The access request includes a request to establish a connection with the medical device 104. The access request may include a command and/or other operation or instruction that controls a function of the medical device 104. For example, the command may control the administration of a treatment or medication, such as dispensing insulin. The access request may identify the medical application 118 of the personal device 102 as a device manager of the medical device 104 and/or the device manager of multiple different medical devices.

The access request may include one or more immutable identifiers of the personal device 102. The one or more immutable identifiers of the personal device 102 may be an International Mobile Equipment Identity (IMEI) number, a phone number, a Bluetooth Low Energy (BLE) Media Access Control (MAC) address. The one or more immutable identifiers are specific identifiers of the personal device 102 that are immutable and/or unchangeable.

The personal device 102 may obtain an authentication request from the medical device 104 (306). The network access device 124 may receive the authentication request from the medical device 104. The encryption engine 116 may decrypt the authentication request and the medical application 118 may present, render or otherwise display the authentication request to the user of the personal device 102.

The authentication request may include a request for one or more authentication factors. The one or more authentication factors may be provided to the medical device 104 to verify, authenticate or authorize the personal device 102 with the medical device 104. After verification, authentication or authorization of the personal device 102 with the medical device 104, the personal device 102 and/or the medical device 104 may establish a secure connection.

The personal device 102 may obtain one or more authentication factors (307). The one or more authentication factors may include a certificate, a password, a hardware authentication token and/or a cloud authentication token. The password may be provisioned at manufacturing, fabrication, packaging or distribution of the medical device 104 and may contain any number of alphanumeric characters of any length, such as a password length of 5 alphanumeric characters or 20 bits. The password may be written within a packaging or within a manual of the medical device 104, such that a user of the medical device 104 and/or the personal device 102 has access to the password. For example, the medical application 118 may present a user interface 136 on the personal device 102 and receive user input through the user interface 136 to obtain the password that was provisioned with the medical device 104 and/or provisioned with the medical application 118, when the medical application 118 was loaded on the personal device 102.

The password may be a zero-knowledge password proof (ZKPP). A zero-knowledge password proof is where one party, such as a user or the medical application 118 on the personal device 102, proves to another party, such as the medical device 104, that it knows a password or key without revealing anything other than the fact that it knows the password to the other party. In some implementations, the password may be lightweight, which minimizes the amount of resources needed by the medical device 104 to verify the password. The lightweight password may be injected or used with an Elliptic Curve Diffie-Hellman pairing algorithm, for example.

The certificate may be a device certificate. The medical application 118 of the personal device 102 may obtain the device certificate from a server 110 through the network 108. The server 110 may perform the functions of a certificate and/or signature authority and sign the device certificate using a private key. A certificate and/or signature authority stores, issues and signs the digital certificates. The server 110 may revoke and/or renew the device certificates of the personal device 102. Upon download of the medical application 118, the medical application 118 may request and/or obtain the device certificate from the server 110 and provision the device certificate during download of the medical application 118.

The device certificate may have one or more immutable identifiers that are bonded to the device certificate. The one or more immutable identifiers may include an International Mobile Equipment Identity (IMEI) number, a phone number, a Bluetooth Low Energy (BLE) Media Access Control (MAC) address, a TrustZone Identifier (ID) or other identifier that is bound and associated with the device certificate. The one or more immutable identifiers may be used by the medical device 104 to verify, authenticate and/or authorize the device certificate and the personal device 102. Other types of authentication factors may include a cloud authentication token and/or a hardware authentication token.

The personal device 102 may obtain the hardware authentication token, such as a password, personal identification number (PIN) or other secret, that originates on the hardware device 106. For example, the hardware device 106 may display a password or PIN, and the personal device 102 may request and receive user input of the password or PIN displayed on the hardware device 106. In another example, the hardware device 106 may be paired with the medical application 118 of the personal device 102 using a certificate.

In some implementations, the personal device 102 may obtain multiple authentication factors, such as a password and a certificate, based on the authentication request to authenticate the personal device 102 with the medical device 104. One or more other devices, such as the hardware device 106, may have one of the one or more authentication factors, such as the hardware authentication token, and provide the one or more authentication factors to the personal device 102 to assist to establish a connection between the personal device 102 and the medical device 104. The personal device 102 may obtain a message and/or a cloud authentication token from the medical device 104 that indicates to the server 110 to verify the personal device 102. The personal device 102 transmits this message and/or cloud authentication token to the server 110 for signature. The server 110 returns the signed message to the medical device 104 to be verified. The message may have been encrypted with the symmetric key shared only between the server 110 and the medical device 104 so no unauthorized application or device may modify the message during transit. The symmetric key may be shared between the medical device 104 and the server 110 during manufacturing, distribution and/or provisioning of the medical device 104.

The personal device 102 may determine whether the one or more authentication factors are valid (308). The personal device 102 may use the server 110 to determine whether the one or more authentication factors are valid. For example, the personal device 102 may analyze the certificate and determine an expiration date of the certificate. In some implementations, the personal device 102 may send the certificate to a server 110, which determines the expiration date of the certificate and a current date and compares the current date with the expiration date to determine the validity of the certificate.

If the authentication factor is not valid, the personal device 102 may obtain a revocation of the authentication factor from the server 110 (310). For example, if the current date of the certificate is past the expiration date, the server 110 may revoke the certificate and send the revocation to the personal device 102, which obtains the revocation. The medical application 118 may delete or otherwise render inoperable the establishment of a communication channel until a new certificate is obtained.

In response to the authentication factor, such as the certificate, being revoked, the personal device 102 may request and/or obtain a renewal of the authentication factor (312). For example, the personal device 102 may request a renewal of the certificate and the server 110 may issue a new certificate and send the new certificate to the personal device 102. The personal device 102 uses the new certificate to replace or renew the expired certificate and store the new certificate in the trusted memory 114.

After the authentication factors has been renewed or if the authentication factor is valid, the personal device 102 may generate a response to the medical device 104 and encrypt the response to the medical device 104 (314). The response may include the one or more authentication factors to send to the medical device 104 to establish the secure connection. The response may include additional information, such as the communication protocol, to establish the connection between the personal device 102 and the medical device 104 using an Elliptic Curve Diffie-Hellman algorithm, for example. The personal device 102 may use the encryption engine 116 to encrypt the response to the medical device 104. The encryption protects the response from unauthorized modification and/or access, which preserves both the confidentiality and integrity of the response when the response is provided to the untrusted components within the untrusted environment 128 for transmission.

The personal device 102 provides or sends the response to the medical device 104 (316). The personal device 102 may use the network access device 124 to send the response to the medical device 104 across a wired or wireless connection. The response includes the one or more authentication factors requested by the medical device 104 for authentication and establishment of the communication channel. Once the one or more authentication factors are validated or verified by the medical device 104, the personal device 102 may receive a signal to establish a connection (318), and in response, establish the secure communication with the medical device 104 (320). The secure communication allows the medical application 118 to communicate with the medical device 104 and provide a secure channel between the medical application 118 and the medical device 104 that protects the integrity and confidentiality of communication within the secure channel.

The personal device 102 may provide commands, instructions and/or other communications within the established communication to control the medical device 104 (322). The commands, instructions and/or other communications may cause the medical device 104 to administer a treatment or medication to a patient, for example.

Figure 4:
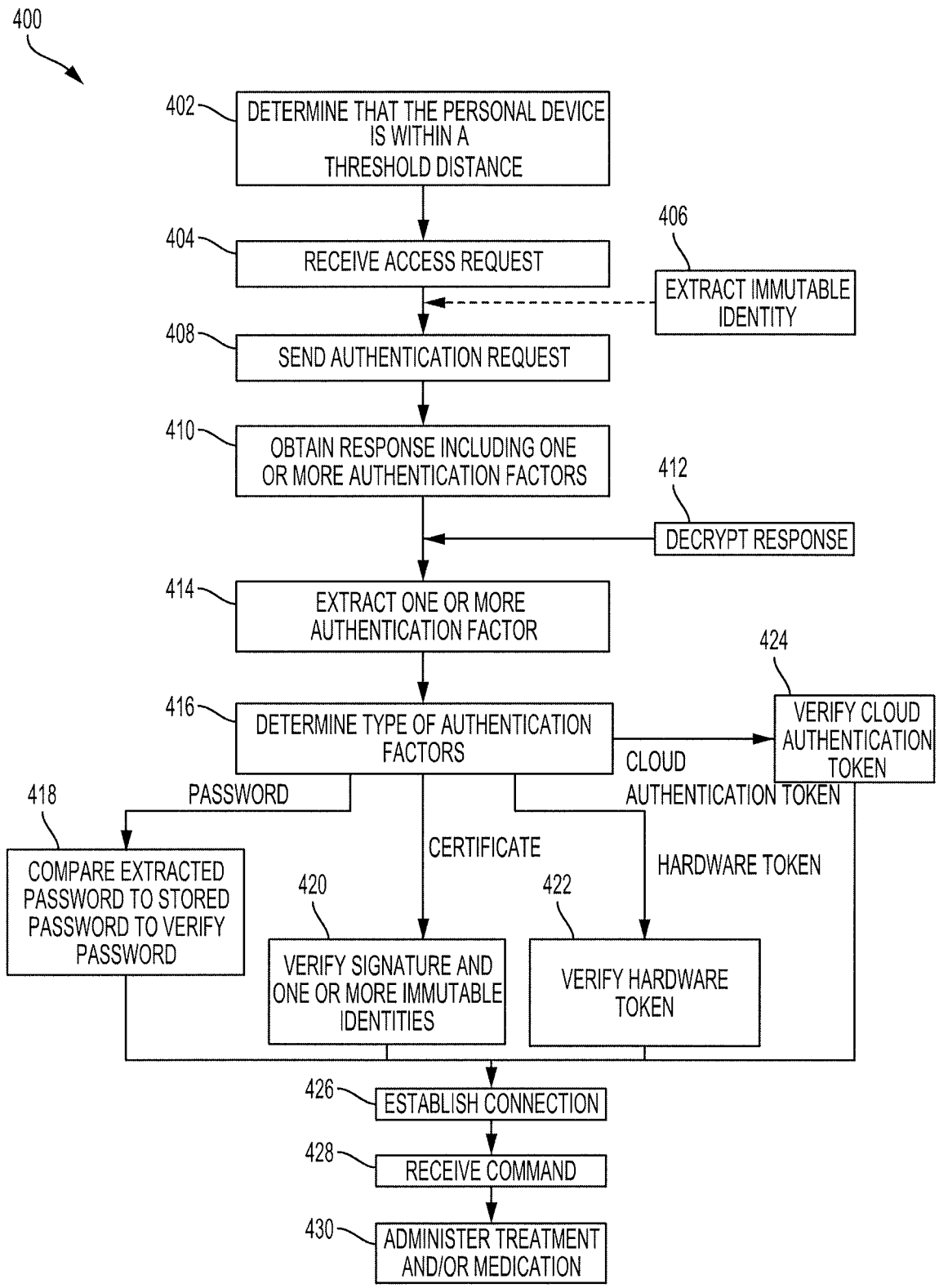
FIG. 4 is a flow diagram of an example process implemented by the medical device to securely connect with the personal device according to an aspect of the invention.

FIG. 4 is a flow diagram of a process 400 implemented on the medical device 104 to securely connect with the personal device 102. The one or more computers or data processing apparatuses, for example, the processor 132 in conjunction with other components, such as the memory 134, of the secure communication system 100 of FIG. 1, appropriately programmed, may establish a secure connection between the personal device 102 and the medical device 104.

The medical device 104 may determine that the personal device 102 is within a threshold distance (402). The medical device 104 may passively discover, scan or search for the personal device 102 to attempt to pair with the personal device 102 when discovered. In some implementations, the medical device 104 is in a passive state awaiting an access request from the medical application 118 on the medical device 104.

The medical device 104 may obtain an access request from the personal device 102 (404). When the medical device 104 obtains the access request from the personal device 102, the medical device 104 may extract from the access request or the protocol used to transmit the access request the one or more immutable identifiers of the personal device 102, such as the IMEI number, the phone number, the BLE MAC address, a TrustZone Identifier (ID) or other identifier (406). The medical device 104 may parse and/or analyze the protocol used to communicate the access request to determine the one or more immutable identifiers of the personal device 102.

In response to obtaining the access request, the medical device 104 may provide or send an authentication request (408). The authentication request may include a request for a single authentication factor and/or a request for multiple authentication factors. The multiple authentication factors may be of different types and requested from the personal device 102, the hardware device 106, the server 110 and/or combinations thereof. That is, the authentication request may request any number of different authentication factors, such as a password, a certificate, a hardware authentication token and/or a cloud authentication token.

For example, the medical device 104 may request the password and/or the certificate from the medical application 118 of the personal device 102. In another example, the medical device 104 may request the hardware authentication token from a separate hardware device 106 in addition or in combination with the request for the password and/or the certificate from the medical application 118 of the personal device 102. The separate hardware device 106 may be provided to the user via a different distribution channel, such as through the mail, to ensure that the original user that received the hardware device 106 is the same user as the user of the personal device 102. In another example, the medical device 104 may send a message with a cloud authentication token to the server 110 via the personal device 102. The medical device 104 and the server 110 may share a symmetric key that is used to encrypt the message so that the personal device 102 or other unauthorized device may not be able to manipulate or modify the message. The message may indicate that the personal device 102 should be an authenticated device.

The medical device 104 may obtain one or more responses that include the one or more authentication factors (410). The medical device 104 may obtain the one or more responses from different devices, such as the personal device 102, the server 110, the hardware device 106 or a combination thereof, based on the type of one or more authentication factors requested. For example, if the medical device 104 sent an authentication request that requested a password and a hardware authentication token, the medical device 104 may anticipate to receive two responses, one response from the medical application 118 on the personal device 102 and another response from the hardware device 106. In another example, the medical device 104 may receive a response from the server 110 that is signed via the personal device 102. The response may indicate that the personal device 102 is authenticated and that the medical device 104 may establish a connection with the personal device 102.

The medical device 104 may decrypt the one or more responses if the one or more responses are encrypted (412). The medical device 104 may use an Elliptic Curve Diffie-Hellman pairing algorithm that is lightweight to minimize the use of resources on the medical device 104 to decrypt the one or more responses.

The medical device 104 may extract the one or more authentication factors from the one or more responses (414). The medical device 104 may determine the type of authentication factor extracted from the one or more responses and authenticate the one or more authentication factors based on the type of authentication factor (416). For example, the medical device 104 may determine whether the authentication factor is a password, a hardware authentication token, a certificate and/or a cloud authentication token.

If the one or more authentication factors include a password, the medical device 104 may compare the extracted password from the one or more responses to a stored password that was provisioned during manufacturing, fabrication and/or distribution (418). If the extracted password and the stored password match, the medical device 104 validates the particular authentication factor of the one or more authentication factors. The medical device 104 may mutually authenticate the extracted password and the stored password to pair the medical device 104 with the medical application 118 on the personal device 102. The medical device 104 and the personal device 102 may use a cryptographic password authenticated pairing and/or key derivation/agreement, e.g., Secure Remote Password (SRP) or Password Authenticated Connection Establishment (PACE) algorithms, to pair the two devices. In some implementations, the medical device 104 uses a lightweight password, which may be injected or used with an Elliptic Curve Diffie-Hellman pairing algorithm, for example, as the cryptographic password authenticated pairing and/or key derivation/agreement.

If the one or more authentication factors include a certificate, the medical device 104 may verify a signature on the certificate and/or verify one or more immutable identifiers to determine the validity of the certificate (420). The medical device 104 may validate the signature and verify the issuer of the certificate to establish a chain of trust with the personal device 102. The medical device 104 may extract one or more immutable identifiers from the certificate and compare the one or more immutable identifiers from the certificate with the one or more immutable identifiers of the personal device 102 and verify that the immutable identifiers match. For example, the medical device 104 may compare and verify that the phone number of the personal device 102 matches a phone number assigned to the certificate. In another example, the medical device 104 may compare and verify that the BLE MAC address, the IMEI number or the TrustZone Identifier (ID) of the personal device 102 matches the BLE MAC address, the IMEI number, and/or the TrustZone Identifier (ID) assigned to the certificate, respectively. In some implementations, the medical device 104 may verify all or any number of the immutable identifiers. If the chain of trust is established and the immutable identifiers match, the medical device 104 validates the certificate and personal device 102.

In some implementations, the medical device 104 may use or query the server 110 to verify the one or more immutable identifiers, such as the TrustZone ID, and/or validate the certificate. The medical device 104 may send the immutable identifier to the server 110, which verifies the immutable identifier, or provides other information such as a phone number, an IMEI number or other identifier to the medical device 104 with which the medical device 104 may use to compare with the one or more immutable identifiers of the personal device 102.

In some implementations, the medical device 104 may provide a medical device certificate of the medical device 104 to the personal device 102. The medical device certificate may be provisioned during manufacturing and stored in flash or a hardware secure element.

If the one or more authentication factors include a hardware authentication token, the medical device 104 may receive the hardware authentication token from a hardware device 106 that is in proximity to the medical device 104 and verify that the hardware authentication token matches a pre-programmed or provisioned token (422). The hardware device 106 may pair the hardware authentication token with the medical application 118 and be used as one of the one or more authentication factors to authenticate the establishment of the secure communication channel between the personal device 102 and the medical device 104. The hardware device 106 may be pre-paired with the medical application 118 of the personal device 102 and may have a hardware authentication token that may include a certificate or require a personal identification number (PIN) or password. The medical device 104 may require that the hardware device 106 with the hardware authentication token be present along with the medical application 118 of the personal device 102 in order to authenticate the medical application 118 of the personal device 102. The medical device 104 may receive the hardware authentication token including the certificate, a PIN, and/or a password from the hardware device 106 along with any other authentication factors from the personal device 102 to authenticate the medical application 118 of the personal device 102. In some implementations, the medical device 104 may use the hardware authentication token to confirm one or more critical commands, such as the administration of a treatment or a medication.

The medical device 104 may receive the hardware authentication token from the hardware device 106 over an "alternate radio," such as Sub-GHz radio or ANT+. The use of an "alternate radio" protects the communication between the hardware device 106 and the medical device 104 to prevent scalable attacks.

If the one or more authentication factors include a cloud authentication token, the medical device 104 may verify the signature on the cloud authentication token to ensure that the message received with the cloud authentication token is valid and from the server 110 (424). The message may indicate that the personal device 102 is authenticated and may establish a communication channel with the medical device 104.

In some implementations, the one or more authentication factors include multiple authentication factors. If the medical device 104 requires multiple authentication factors to establish a secure connection, the medical device 104 must validate the multiple authentication factors prior to establishing the secure connection. That is, all the required authentication factors must be verified. For example, if the medical device 104 requires a valid password and a valid certificate, both the password and the certificate must be validated prior to establishing the secure connection with the personal device 102.

Once the medical device 104 authenticates the one or more authentication factors, the medical device establishes a connection with the medical application 118 of the personal device 102 (426). The medical device 104 may receive a command, an instruction or other communication from the medical application 118 that controls the medical device 104, which may require additional verification of another authentication factor (428). The medical device 104 administers treatment or medication based on the command, the instruction or other communication from the medical application 118 (430).

Where used throughout the specification and the claims, "at least one of A or B" includes "A" only, "B" only, or "A and B." Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A mobile device for providing secure communication, comprising:
a trusted environment having:
a memory that is configured to store an application that manages or controls a medical device, and
an encryption engine that is configured to encrypt communications through an untrusted environment of the mobile device and to the medical device; and
one or more processors configured to perform operations of the application that execute within the trusted environment, the operations comprising:
sending an access request to connect with the medical device and that identifies the application as the application that manages or controls the medical device,
receiving an authentication request from the medical device that requests the application to provide one or more authentication factors including a zero-knowledge password proof that was provided when the application was loaded on the mobile device or with the medical device,
obtaining the zero-knowledge password proof,
sending the zero-knowledge password proof to the medical device, and
establishing a communication channel with the medical device.

2. The mobile device of claim 1, further comprising the untrusted environment, wherein the untrusted environment has another memory, wherein the one or more processors perform other operations that execute within the untrusted environment.

3. The mobile device of claim 2, wherein the trusted environment has a trusted execution space that is logically or physically separated from the untrusted environment and secures the application from security vulnerabilities residing on the mobile device.

4. The mobile device of claim 1, wherein the operations within the trusted environment further comprise:
encrypting the zero-knowledge password proof prior to sending the zero-knowledge password proof to the medical device.

5. The mobile device of claim 1, wherein the zero-knowledge password proof is sent to the medical device without revealing any other information.

6. The mobile device of claim 1, wherein the authentication request from the medical device requests the application to provide a certificate or cloud authentication token, wherein the operations further comprise:
obtaining from a server the certificate or the cloud authentication token;
sending the certificate or the cloud authentication token to the medical device; and
establishing communication with the medical device further using the certificate or the cloud authentication token.

7. The mobile device of claim 6, wherein the certificate includes an immutable identifier that is verified by the medical device, wherein the certificate is signed by the server using a private key or other signature authority.

8. The mobile device of claim 7, wherein the immutable identifier includes at least one of an International Mobile Equipment Identity (IMEI) number, a phone number, a Bluetooth Low Energy (BLE) Media Access Control (MAC) address, or a TrustZone Identifier (ID).

9. The mobile device of claim 6, wherein the cloud authentication token is provisioned during manufacturing, distribution or packaging.

10. The mobile device of claim 1, further comprising a secure element, wherein the trusted environment is within the secure element, wherein the one or more processors are further configured to perform operations comprising:
obtaining, from a server, a certificate;
storing the certificate in the memory;
revoking the certificate after a period of time; and
renewing the certificate with the server after the certificate is revoked.

11. A medical device, comprising:
a memory; and
one or more processors configured to execute instructions stored in the memory and perform operations comprising:
discovering a mobile device when the mobile device is within a threshold distance of the medical device,
sending an authentication request to the mobile device,
receiving a response to the authentication request that includes one or more authentication factors including at least one of a zero-knowledge password proof, a certificate or a cloud authentication token from the mobile device,
determining a type of authentication factor that is included in the response,
authenticating the one or more authentication factors including the at least one of the zero-knowledge password proof, the certificate or the cloud authentication token from the mobile device based on the type of authentication factor included in the response, and establishing communication with the mobile device.

12. The medical device of 11, wherein receiving the at least one of the zero-knowledge password proof, the certificate or the cloud authentication token from the mobile device includes receiving the zero-knowledge password proof and the certificate, wherein the certificate includes an immutable identity.

13. The medical device of claim 12, wherein authenticating the one or more authentication factors including at least one of zero-knowledge password proof, the certificate or the cloud authentication token from the mobile device includes:
comparing the immutable identity included in the certificate to an identity of the mobile device or information stored on a server; and
verifying that the certificate is valid based on the comparison.

14. The medical device of claim 13, wherein the immutable identity is at least one of an International Mobile Equipment Identity (IMEI) number, a phone number, a Bluetooth Low Energy (BLE) Media Access Control (MAC) address, or a TrustZone Identifier (ID).

15. The medical device of claim 11, wherein authenticating the one or more authentication factors including the at least one of the zero-knowledge password proof, the certificate or the cloud authentication token from the mobile device includes authenticating the zero-knowledge password proof and the certificate.

16. A method for securely communicating between a medical device and an application on a personal device in a secure computing environment, comprising:
discovering, using a network access device of the medical device, the personal device when the personal device is within a threshold distance of the medical device;
receiving, by the network access device of the medical device, an access request that identifies the application as the application that manages or controls the medical device after the personal device is discovered;
in response to receiving the access request, sending, by a processor of the medical device, an authentication request that requests a plurality of authentication factors;
receiving, by the processor of the medical device, the plurality of authentication factors;
determining, by the processor of the medical device, a type of authentication factor that is received among the plurality of authentication factors;
authenticating, by the processor of the medical device, the plurality of authentication factors based on the type of authentication factor;
establishing, by the processor of the medical device and the application on the personal device, a chain of trust between the medical device and the personal device; and
establishing, by the processor of the medical device and the application on the personal device, a secure communication channel between the medical device and the personal device based on the chain of trust.

17. The method of claim 16, wherein the plurality of authentication factors further include at least one of a hardware token, a cloud authentication token, or a zero-knowledge password proof.

18. The method of claim 17, wherein establishing, by the processor and the application on the personal device, the chain of trust between the medical device and the personal device includes:
sending, by the processor of the medical device via the personal device, a message to a server, the message including a cloud authentication token and a request to authenticate the personal device;
generating and signing, by the server, a response that includes an authorization of the personal device;
sending, by the server, the response to the medical device via the personal device;
verifying, by the processor of the medical device, the signature of the response; and
authenticating, by the processor of the medical device, the personal device.

19. The method of claim 18, wherein the personal device is a smartphone that is configured to run a plurality of applications including the application.

20. The method of claim 16, wherein the plurality of authentication factors includes a first authentication factor from a tamper-proof secure element, wherein establishing the chain of trust is based on the first authentication factor.

* * * * *